(12) United States Patent
Schmithorst et al.

(10) Patent No.: US 12,262,985 B2
(45) Date of Patent: Apr. 1, 2025

(54) OPTIMIZING MAGNETIC RESONANCE IMAGING PROTOCOLS FOR INCREASED SPEED

(71) Applicant: University of Pittsburgh—Of the Commonwealth System of Higher Education, Pittsburgh, PA (US)

(72) Inventors: Vanessa Schmithorst, Cheswick, PA (US); Rafael Ceschin, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 26 days.

(21) Appl. No.: 18/019,922

(22) PCT Filed: Aug. 6, 2021

(86) PCT No.: PCT/US2021/045002
§ 371 (c)(1),
(2) Date: Feb. 6, 2023

(87) PCT Pub. No.: WO2022/032133
PCT Pub. Date: Feb. 10, 2022

(65) Prior Publication Data
US 2023/0293037 A1  Sep. 21, 2023

Related U.S. Application Data

(60) Provisional application No. 63/061,896, filed on Aug. 6, 2020.

(51) Int. Cl.
*A61B 5/055* (2006.01)
*G01R 33/54* (2006.01)
*G06T 7/00* (2017.01)

(52) U.S. Cl.
CPC ............ *A61B 5/055* (2013.01); *G01R 33/543* (2013.01); *G06T 7/00* (2013.01); *G06T 2207/10088* (2013.01)

(58) Field of Classification Search
CPC ........ A61B 5/055; G01R 33/543; G06T 7/00; G06T 2207/10088
See application file for complete search history.

(56) References Cited

U.S. PATENT DOCUMENTS 8,975,892 B2 * 3/2015 Flammang ............. G01R 33/50
324/309
10,441,311 B2 * 10/2019 Smith ............ A61B 17/320758
(Continued)

FOREIGN PATENT DOCUMENTS

JP          2634900        7/1997
WO     WO 2015/140277     9/2015

OTHER PUBLICATIONS

International Preliminary Report on Patentability in International Appln. No. PCT/US2021/45002, mailed on Feb. 16, 2023, 12 pages.
(Continued)

*Primary Examiner* — Gregory H Curran
(74) *Attorney, Agent, or Firm* — Fish & Richardson P.C.

(57) ABSTRACT

In an example, a computer system receives first data regarding a magnetic resonance imaging (MRI) protocol for obtaining image information regarding a subject, and determines a plurality of parameter sets for performing the MRI protocol. Each of the parameter sets includes an indication of one or more parameters associated with the MRI protocol, and for each of the one more parameters, an indication of a respective parameter value. The computer system determines, for each of the parameter sets, a respective first quality metric, and selects a particular one of the parameter sets based on the first quality metrics. The computer system provides instructions for performing the MRI protocol to a (Continued)

magnetic resonance (MR) scanner. The instructions include an indication of the selected parameter set.

35 Claims, 6 Drawing Sheets

(56) References Cited

U.S. PATENT DOCUMENTS

| | | |
|---|---|---|
| 2003/0109781 A1 | 6/2003 | Zhang |
| 2014/0348406 A1 | 11/2014 | Cowan et al. |
| 2016/0018498 A1 | 1/2016 | Boernert et al. |
| 2016/0146910 A1 | 5/2016 | Kaneko et al. |
| 2017/0156630 A1 | 6/2017 | Gabr et al. |
| 2019/0056470 A1 | 2/2019 | Wang |

OTHER PUBLICATIONS

International Search Report and Written Opinion in International Appln. No. PCT/US2021/45002, mailed on Jan. 11, 2022, 15 pages.
Jaspan et al., "Compressed sensing MRI: a review of the clinical literature," Br. J. Radiol., Dec. 2015, 88(1056):20150487, 12 pages.
Ma et al., "Magnetic resonance fingerprinting," Nature, Mar. 2013, 495(7440):187-192.

\* cited by examiner

OPTIMIZING MAGNETIC RESONANCE IMAGING PROTOCOLS FOR INCREASED SPEED

CROSS-REFERENCE TO RELATED APPLICATIONS

This application is a National Stage application under 35 U.S.C. § 371 of International Application No. PCT/US2021/045002, having an International Filing Date of Aug. 6, 2021, which claims the benefit of U.S. Provisional Application Ser. No. 63/061,896, filed Aug. 6, 2020. The disclosure of the prior application is considered part of (and is incorporated by reference in) the disclosure of this application.

TECHNICAL FIELD

This disclosure relates to magnetic resonance imaging.

BACKGROUND

Magnetic resonance imaging (MRI) is a medical imaging technique used to form images of the anatomy and the physiological processes of a subject based on the subject's response to magnetic fields. As an example, a magnetic resonance (MR) scanner can generate magnetic fields, magnetic field gradients, and radio waves within a bore of the MR scanner, measure the properties of a subject within the bore, and generate one or more images based on the measurements.

SUMMARY

In an aspect, a method includes receiving, by a computer system, first data regarding a magnetic resonance imaging (MRI) protocol for obtaining image information regarding a subject. The computer system determines multiple parameter sets for performing the MRI protocol, where each of the parameter sets includes (i) an indication of one or more parameters associated with the MRI protocol, and (ii) for each of the one more parameters, an indication of a respective parameter value. For each of the parameter sets, a respective first quality metric can be determined. The computer system then selects a particular one of the parameter sets based on the first quality metrics, and provides instructions for performing the MRI protocol to a magnetic resonance (MR) scanner, where the instructions include an indication of the selected parameter set.

Implementations of this aspect can include one or more of the following features.

In some implementations, the first data can include at least one of an indication of a medical condition of the subject or an indication of a type of image contrast associated with the MRI protocol.

In some implementations, the first data can include an indication of a type of image contrast associated with the MRI protocol.

In some implementations, the type of image contrast can be at least one of a T1-weighted contrast, a T2-weighted contrast, or a diffusion-weighted contrast.

In some implementations, the first data can include an indication of a magnetic resonance (MR) pulse sequence associated with the MRI protocol.

In some implementations, the one or more parameters associated with the MRI protocol can include at least one of a field of view, a matrix size, a slice thickness, a repetition time, an echo time, an inversion time, a flip angle, a magnetic gradient strength, a magnetic gradient duration, a radio frequency (RF) transmit power, a time-bandwidth product, or an averaging of acquired data.

In some implementations, the one or more parameter associated with the MRI protocol can include a shape of a pulse in a pulse sequence of the MRI protocol.

In some implementations, the shape of the pulse can include at least one of a duration of the pulse, or a magnitude of the pulse.

In some implementations, the one or more parameters associated with the MRI protocol can include at least one of a number of slabs from which to obtain the image information regarding the subject, an acquisition sequence for the slabs, a spacing between the slabs, a thickness of the slabs, an oversampling factor for the slabs, or a number of sample points in a phase-encoding direction.

In some implementations, determining the first quality metrics can include, for each of the parameter sets: determining an estimated signal response of the subject responsive to performing the MRI protocol according to that parameter set; determining one or more first properties of the estimated signal response; determining an estimated duration of time for performing the MRI protocol according to that parameter set; and determining the first quality metric for that parameter set based on the one or more first properties of the estimated signal response and the estimated duration of time.

In some implementations, the one or more first properties can include at least one of a contrast to noise ratio of the estimated signal response or a signal to noise ratio of the estimated signal response.

In some implementations, the estimated signal response can be determined based on a set of differential equations.

In some implementations, the set of differential equations can include Bloch equations.

In some implementations, the first quality metrics can be determined based on a cost function.

In some implementations, the cost function can include a plurality of components. Further, the components can include, for each of the parameter sets, at least one of: a first component corresponding to a fidelity of data acquired according to that parameter sets, a second component corresponding to a perturbation of proton spins outside a region of interest specified by that parameter set, or a second component corresponding to an excitation of proton outside the region of interest specified by that parameter set.

In some implementations, the cost function can include a weighted sum of the components.

In some implementations, determining, for each of the parameter sets, a respective first quality metric can include determining, for each of the parameter sets, an output of the cost function for that parameter set.

In some implementations, selecting the particular one of the parameter sets can include selecting, from among the parameter sets, the parameter set associated with the lowest output of the cost function.

In some implementations, selecting the particular one of the parameter sets can include selecting, from among the parameter sets, the parameter set associated with the lowest outputted value of the cost function.

In some implementations, selecting a particular one of the parameter sets can include selecting the parameter set having the greatest first quality metric among the first quality metrics.

In some implementations, selecting a particular one of the parameter sets can include selecting a parameter set having a first quality metric that exceeds a threshold value.

In some implementations, the method can further include determining, by the computer system, second data regarding a feature space associated with the MRI protocol; determining, by the computer system, multiple acquisition spaces for acquiring signal measurements according to the MRI protocol; determining, by the computer system for each of the acquisition spaces, a respective second quality metric regarding the feature space; and selecting, by the computer system, one of the acquisition spaces based on the second quality metrics. The instructions can further include an indication of the selected acquisition space, and an indication of an association between the selected acquisition space and the feature space.

In some implementations, the feature space can include at least one of one or more anatomical features of the subject or one or more types of tissue of the subject.

In some implementations, at least one of the acquisition spaces can include a respective pattern of sample points in k-space.

In some implementations, at least one of the acquisition spaces can include a respective pattern of sample points acquired using one or more non-linear imaging gradients or transmit pulses.

In some implementations, determining the second quality metrics can include, for each of the acquisition spaces: obtaining image data corresponding to a performance of the MRI protocol according to that acquisition space; determining one or more second properties of the image data with respect to the feature space; and determining the second quality metric for that acquisition space based on the one or more second properties of the image data.

In some implementations, the one or more second properties of the image data can include at least one of a contrast to noise ratio with respect to the feature space or a signal to noise ratio with respect to the feature space.

In some implementations, the one or more second properties of the image data can include a qualitative score regarding the feature space.

In some implementations, the qualitative score can be received from one or more users.

In some implementations, selecting one of the acquisition spaces can include selecting the acquisition space having the greatest second quality metric among the second quality metrics.

In some implementations, selecting one of the acquisition spaces can include selecting an acquisition space having a second quality metric that exceeds a threshold value.

In another aspect, a method includes receiving, by a computer system, first data regarding a magnetic resonance imaging (MRI) protocol for obtaining image information regarding a subject; determining, by the computer system, second data regarding a feature space associated with the MRI protocol; determining, by the computer system, multiple acquisition spaces for acquiring signal measurements according to the MRI protocol; determining, by the computer system for each of the acquisition spaces, a respective quality metric regarding the feature space; selecting, by the computer system, one of the acquisition spaces based on the quality metrics; and providing, by the computer system, instructions for performing the MRI protocol to a magnetic resonance (MR) scanner. The instructions include an indication of the selected acquisition space, and an indication of an association between the selected acquisition space and the feature space.

Implementations of this aspect can include one or more of the following features.

In some implementations, the feature space can include at least one of one or more anatomical features of the subject or one or more types of tissue of the subject.

In some implementations, at least one of the acquisition spaces can include a respective pattern of sample points in k-space.

In some implementations, at least one of the acquisition spaces can include a respective pattern of sample points acquired using one or more non-linear imaging gradients or transmit pulses.

In some implementations, determining the quality metrics can include, for each of the acquisition spaces: obtaining image data corresponding to a performance of the MRI protocol according to that acquisition space; determining one or more properties of the image data with respect to the feature space; and determining the quality metric for that acquisition space based on the one or more properties of the image data.

In some implementations, the one or more properties of the image data can include at least one of a contrast to noise ratio with respect to the feature space or a signal to noise ratio with respect to the feature space.

In some implementations, the one or more properties of the image data can include a qualitative score regarding the feature space.

In some implementations, the qualitative score can be received from one or more users.

In some implementations, selecting one of the acquisition spaces can include selecting the acquisition space having the greatest quality metric among the quality metrics.

In some implementations, selecting one of the acquisition spaces can include selecting an acquisition space having a quality metric that exceeds a threshold value.

In another aspect, a method includes receiving, by a first computer system, instructions for performing an MRI protocol from a second computer system. The instructions include an indication of a particular parameter set selected from among multiple parameter sets by the second computer system. Selecting the particular parameter set includes determining the multiple parameter sets for performing the MRI protocol, where each of the parameter sets includes an indication of one or more parameters associated with the MRI protocol, and for each of the one more parameters, an indication of a respective parameter value; determining, for each of the parameter sets, a respective first quality metric; and selecting the particular one of the parameter sets based on the first quality metrics. The method also includes causing, by the first computer system, a magnetic resonance (MR) scanner to perform the MRI protocol according to the instructions.

In some implementations, the instructions can also include an indication of a particular acquisition space for performing the MRI protocol, and an indication of an association between the particular acquisition space and a feature space associated with the MRI protocol. Selecting the particular parameter set can include determining second data regarding the feature space; determining multiple acquisition spaces for acquiring signal measurements according to the MRI protocol; determining, for each of the acquisition spaces, a respective second quality metric regarding the feature space; and selecting the particular acquisition space from among the multiple acquisition spaces based on the second quality metrics.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

A magnetic resonance imaging (MRI) training platform can facilitate the development of efficient and effective MRI protocols for investigating the anatomy and physiological processes of a subject (e.g., a human or other mammal). As an example, an MRI training platform can receive data regarding characteristics of a subject, a type of information that is to be obtained regarding the subject using an MRI protocol, and any constraints regarding the performance of the MRI protocol. Based on this data, the MRI training platform can optimize one or more parameters for performing the MRI protocol, such that the MRI protocol can be performed in a time-efficient manner and without negatively impacting the diagnostic quality of the resulting images. Further, the MRI training platform can direct a magnetic resonance (MR) scanner to perform the optimized MRI protocol and/or store data records regarding the optimized MRI protocol for future retrieval.

The techniques described herein can provide various technical benefits. For example, in some implementations, the techniques described herein can enable MRI protocols to be performed more quickly (e.g., compared to MRI protocols that have not been optimized by the MRI training platform). This can be beneficial, for example, in enabling the MR scanner to image a greater number of subjects during a particular period of time and/or enabling subjects to be imaged more thoroughly during an imaging session (e.g., by performing a greater number of MRI protocols during the image session than might otherwise be possible). As another example, in some implementations, the techniques describe herein can also improve patient comfort (e.g., by shortening the amount of time that a patient is required to remain in the bore of an MR scanner, which may be narrow and uncomfortable). As another example, in some implementations, the techniques described herein can also improve the diagnostic quality of images that are produced by the MRI protocol (e.g., by enhancing the contrast of features of interest in the subject relative to other features), thereby improving the accuracy of medical diagnoses.

Figure 1:
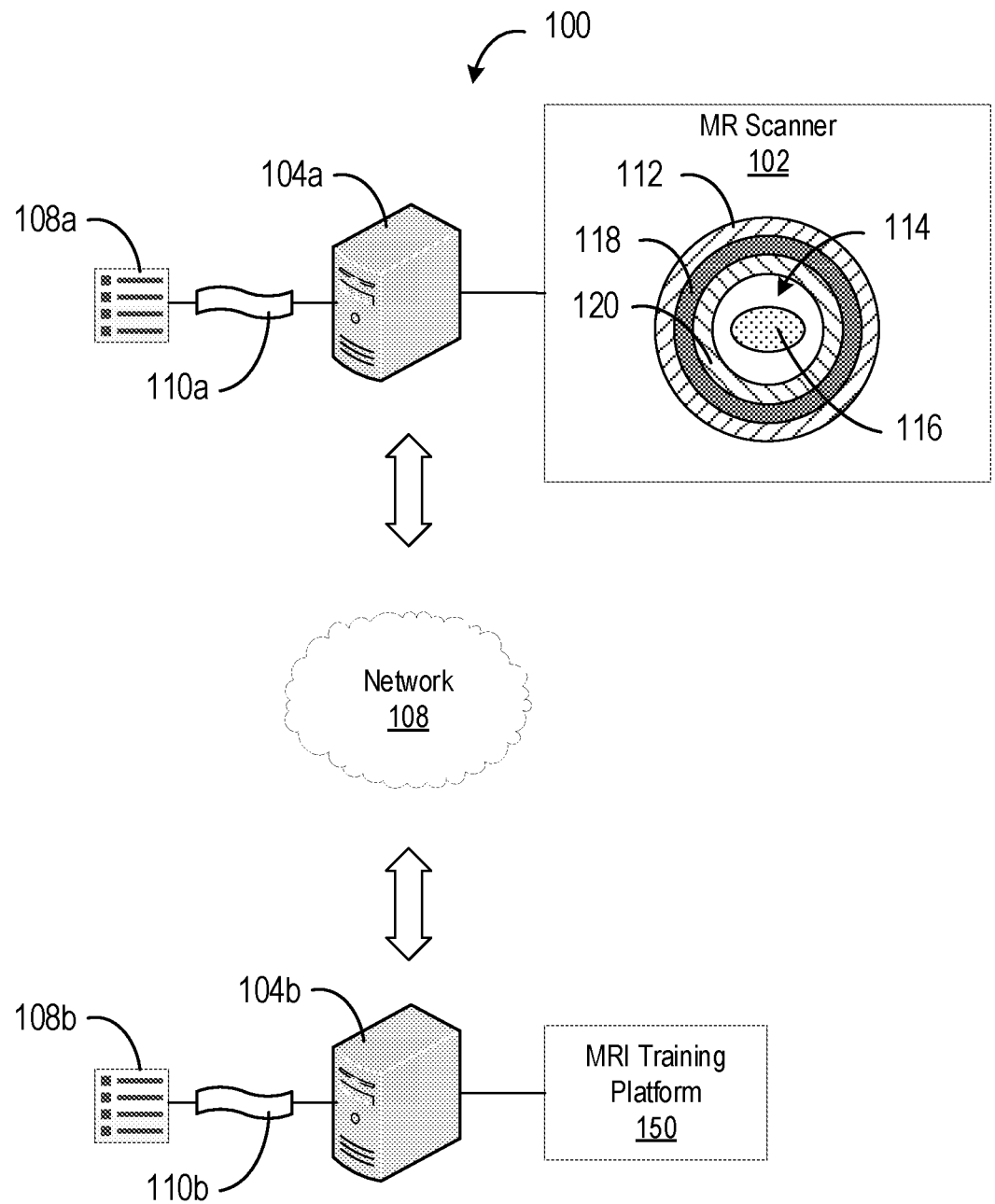
FIG. 1 is a diagram of an example system for obtaining MR images of a subject.

An example system 100 for obtaining MR images of a subject is shown in FIG. 1. The system 100 includes a MR scanner 102, a computer system 104a for controlling the operation of the MRI scanner 102, and a MRI training platform 150 maintained on a computer system 104b. The computer systems 104a and 104b are communicatively connected to one another by direct connection or through a network 108.

The MR scanner 102 is a system for generating images of the anatomy and physiological processes of a subject based on the subject's response to magnetic fields. In general, in MRI, hydrogen nuclei (i.e., protons) present in the tissues of a subject create a signal that is processed to form an image of the subject in terms of the density of those nuclei in a specific region. As the protons are affected by fields from other atoms to which they are bonded, it is possible to separate responses from hydrogen in specific compounds.

To perform an imaging protocol, a subject is positioned within the MR scanner 102, which forms a strong magnetic field around the area to be imaged (e.g., 1.5 T, 3 T, etc.). For example, the MR scanner 102 can include a superconducting magnet 112 that is configured to induce a magnetic field through a bore 114 of the magnet 112, within which a subject 116 is positioned. Further, energy from an oscillating magnetic field is temporarily applied to the subject at the appropriate resonance frequency (e.g., the resonance frequency of the hydrogen nuclei of the subject, in response of the magnetic field). Scanning with gradient coils 118 cause a selected region of the subject to experience the exact magnetic field required for the energy to be absorbed. The excited atoms emit a radio frequency (RF) signal, which is measured by a receiving coil 120. The RF signal may be processed (e.g., by the computer system 104a) to deduce position information by identifying the changes in RF level and phase caused by varying the local magnetic field using the gradient coils 118. The contrast between different tissues is determined by the rate at which excited atoms return to the equilibrium state.

The computer system 104a is communicatively coupled to the MR scanner 102, and is configured to control the operation of the MR scanner 102 and/or to process data generated by the MR scanner 102. For example, the computer system 104a can instruct the MR scanner 102 to generate magnetic fields and measure RF signals emitted by the subject according to a particular MRI protocol (e.g., a sequence of commands for generating specific types of images of the subject). As another example, the computer system 104a can receive data regarding the measured RF signals, and generate one or more images based on the data.

As described above, the MRI training platform 150 can facilitate the development of efficient and effective MRI protocols for generating images using the MR scanner 102. As an example, the MRI training platform 150 can receive data regarding the characteristics of the subject, the type of information that is to be obtained regarding the subject using the MRI protocol, and any constraints regarding the performance of the MRI protocol. Based on this data, the MRI training platform can optimize one or more parameters for performing the MRI protocol. Further, the MRI training platform 150 can direct the MR scanner 102 to perform the optimized MRI protocol (e.g., by transmitting data regarding the optimized MRI protocol to the computer system 104a). Further, the MRI training platform 150 can store data records regarding the optimized MRI protocol for future retrieval. Further details regarding the MRI training platform 150 are described below.

Each of the computer systems 104a and 104b can include one or more electronic devices that are configured to view, process, and transmit, and/or receive data. Examples of the computer systems 104a and 104b include computers (such as desktop computers, notebook computers, server systems, etc.), mobile computing devices (such as cellular phones, smartphones, tablets, personal data assistants, notebook computers with networking capability), and other computing devices capable of transmitting and receiving data from the network 108. The computer systems 104a and 104b can include devices that operate using one or more operating system (e.g., Microsoft Windows, Apple macOS, Linux, Unix, Google Android, Apple iOS, etc.) and/or architectures (e.g., x86, PowerPC, ARM, etc.) In some implementations, one or more of the computer systems 104a and 104b need not be located locally with respect to the rest of the system 100, and one or more of the computer systems 104a and 104b can be located in one or more remote physical locations.

Each the computer systems 104a and 104b includes a respective user interface 108a and 108b. Users interact with the user interfaces 108a and 108b to view data (e.g., data on the computer system 104a, the computer system 104b, the MR scanner 102, and/or the MRI training platform 150). Users also interact with the user interfaces 108a and 108b to transmit data to other devices (e.g., to the computer system 104a, the computer system 104b, the MR scanner 102, and/or the MRI training platform 150). Users interact with the user interfaces 108a and 108b to issue commands 110a and 110b, respectively. Commands 110a and 110b can be, for example, any user instruction to the computer system 104a, the computer system 104b, the MR scanner 102, and/or the MRI training platform 150. In some implementations, a user can install a software application onto the computer systems 104a and/or 104b to facilitate performance of these tasks.

The network 108 can be any communications network through which data can be transferred and shared. For example, the network 108 can be a local area network (LAN) or a wide-area network (WAN), such as the Internet. The network 108 can be implemented using various networking interfaces, for instance wireless networking interfaces (such as Wi-Fi, Bluetooth, or infrared) or wired networking interfaces (such as Ethernet or serial connection). The network 108 also can include combinations of more than one network, and can be implemented using one or more networking interfaces.

In FIG. 1, the computer systems 104a and 104b are illustrated as respective single components. However, in practice, the computer systems 104a and 104b can be implemented on one or more computing devices (e.g., each computing device including at least one processor such as a microprocessor or microcontroller). As an example, the computer system 104b can be a single computing device that is connected to the network 108, and the MRI training platform 150 can be maintained and operated on the single computing device. As another example, the computer system 104b can include multiple computing devices that are connected to the network 108, and the MRI training platform 150 can be maintained and operated on some or all of the computing devices. For instance, the computer system 104b can include several computing devices, and the MRI training platform 150 can be distributive on one or more of these computing devices.

Figure 2:
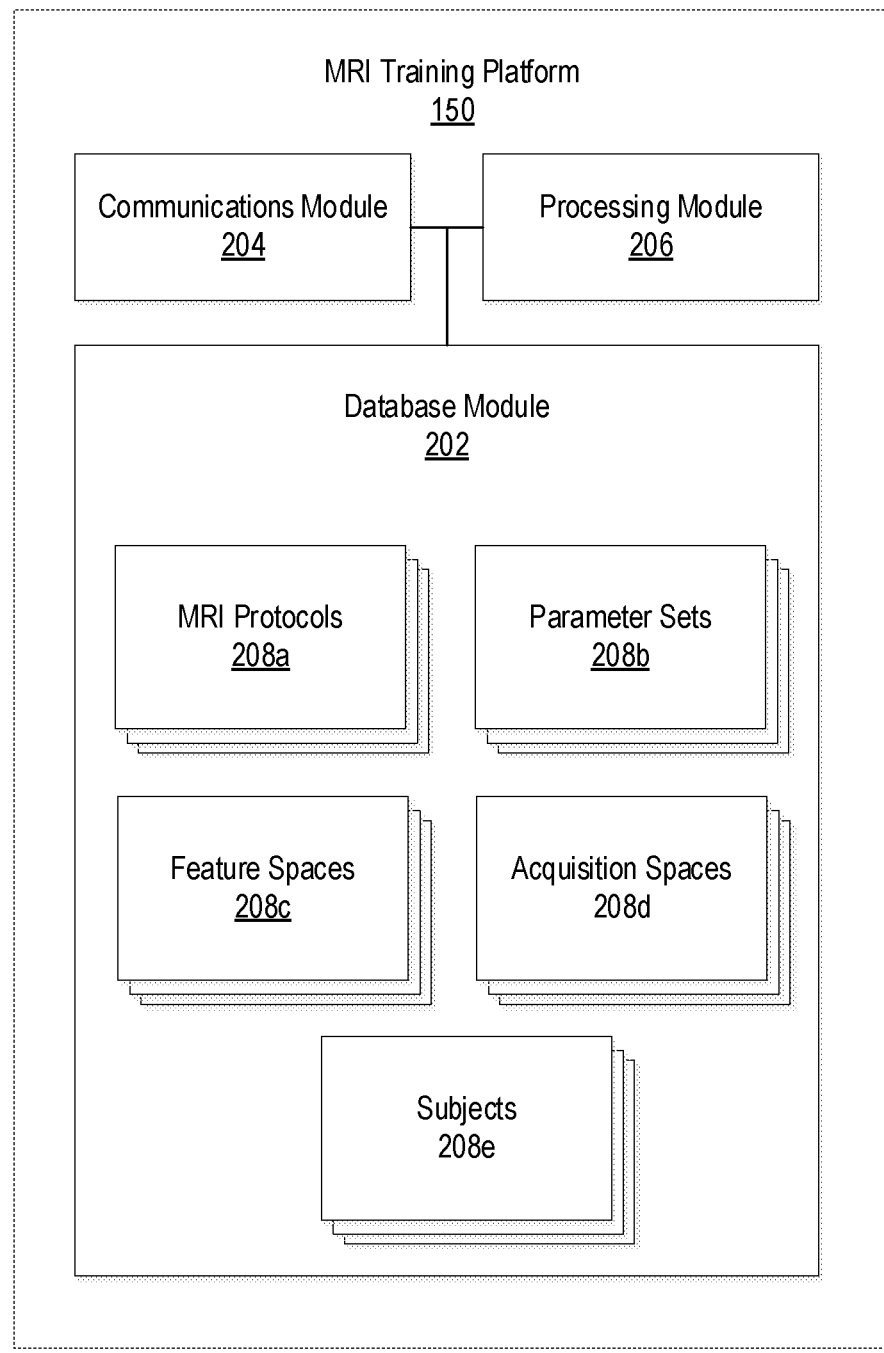
FIG. 2 is a diagram of an example MRI training platform.

FIG. 2 shows various aspects of the MRI training platform 150. The MRI training platform 150 includes various modules that perform particular functions related to the operation of the system 100. For example, the MRI training platform 150 can include a database module 202, a communications module 204, and a processing module 206.

The database module 202 maintains information related to optimizing MRI protocols for use with the MR scanner 102. For instance, the database module 202 can store data regarding the characteristics of the subject, the type of information that is to be obtained regarding the subject using the MRI protocol, and any constraints regarding the performance of the MRI protocol.

As an example, the database module can store data 208a regarding one or more MRI protocols that can be performed using the MR scanner 102. The data 208a can include, for instance, information regarding the type of image contrast that is generated by each MRI protocol (e.g., T1-weighted contrast, T2-weighted contrast, diffusion-weighted contrast, and/or any other type of contrast). Further, the data 208a can include, for each MRI protocol, information regarding how the components of the MR scanner 102 can be operated to generate magnetic fields and measure RF signals, and information regarding the sequence in which the magnetic fields are generated and RF the signals are measured (e.g., information regarding the "pulse sequences" for each MRI protocol).

As another example, the database module 202 can store data 208b regarding sets of parameters that can be used to perform each of the MRI protocols. For instance, the parameters can include a field of view, a matrix size, a slice thickness, a number of slices, a repetition time (TR), an echo time (TE), an inversion time (TI), a flip angle (FA), a magnetic gradient strength, a magnetic gradient duration, a RF transmit power, and/or a time-bandwidth product (TBW) associated with one or more of the MRI protocols. Further, the data 208b can include, for each parameter set, different respective values for each of those parameters.

Further, the data 208b can include parameters regarding the shape of one or more pulses in a pulse sequence. As examples, the data 208b can specify the height, width, amplitude, and/or duration of each pulse. As another example, the data 208b can specify the profile or curve of a pulse over time (e.g., selected from a set of multiple pre-defined pulse profiles or curves available to the system.

Further, for at least some MRI protocols, the data 208b can include parameters specifying that data from a particular slice be averaged together in a particular manner. For example, if a slice has a width of 20 mm in an x-direction, a height of 20 mm in a y-direction, and a thickness of 1 mm in a z-direction, the MRI protocol can specify that data be averaged along the z-direction (e.g., to generate 20 mm×20 mm imaging data according to a x-y plane). In some implementations, the parameters can also indicate the number of data points that are obtained for each slice.

In some implementations, an MRI protocol can specify that the MRI scanner 102 obtain information regarding multiple portions of a subject in a sequence. Each of these portions may be referred to as a "slab." As an example, a multi-slab MRI protocol can specify that the MRI scanner 102 obtain information regarding a first portion of the subject (e.g., a first slab of the subject), and subsequently obtain information regarding a second different portion of the subject (e.g., a second slab of the subject). The database module 202 can store data 208b regarding sets of parameters for performing a multi-slab MRI protocol. For instance, for a multi-slab MRI protocol, the parameters can include the number of slabs for which information will be obtained, the sequence in which the slabs are acquired, the time between the acquisition of slabs (e.g., the time between the end of acquiring data for one slab and the beginning of acquiring data for the next slab in the sequence), the locations of the slabs on the subject (e.g., according to a spatial coordinate system), the locations of the slabs relative to one another (e.g., the spatial separation or spacing between adjacent slabs), the number of slices in each slab, the orientation and spatial distribution of slices in each slab, the thickness of each slab, the oversampling factor for each slab, and/or the number of sample points for each slab (e.g., in a phase-encoding direction). Further, the parameters can indicate whether any slabs are acquired multiple times, either in a sequence or interleaved with the acquisition of other slabs.

In some implementations, a multi-slab MRI protocol can specify that data for multiple slabs be acquired by shifting the range of frequencies and/or phases of the excitation pulses between slabs. This can be beneficial, for example, in increasing the overall signal to noise ratio (SNR) of the acquired signals. For these types of MRI protocols, the data 208b can include parameters such as the shift factor between slabs (e.g., the magnitude of the shift) and the direction of the shift (e.g., in the direction of frequency encoding and/or in the direction of phase encoding).

In some implementations, an MRI protocol can specify that the MRI scanner 102 obtain samples regarding a subject according to an oversampling technique, whereby the sampling frequency is increased compared to that of a non-oversampled technique. In some implementations, the sampling frequency can be selected such that it is at least twice the frequency of each frequency component of the incoming signal. This can be useful, for example, in reducing aliasing, wrap around effects, and/or other artifacts in the reconstructed images. For these types of MRI protocols, the data 208b can include parameters specifying the direction of the oversampling (e.g., in the direction of frequency encoding and/or in the direction of phase encoding), the sampling frequency, the sampling pattern (e.g., in k-space, as discussed in further detail below), and/or the oversampling factor.

Further, according to some oversampling techniques, an MRI protocol can specify that MRI scanner 102 excite an extended portion of the subject that includes a slab of interest, as well as additional regions surrounding the slab. Further, the multi-slab MRI protocol can specify that that MRI scanner 102 obtain samples from the extended portion. Further, the multi-slab MRI protocol can specify that an image be reconstructed for only a subset of the sampled data (e.g., sampled data for the slab of interest, and not the additional regions surrounding the slab). This can be useful, for example, in further reducing artifacts and/or wrap-around effects in the images. For these MRI protocols, the data 208b can include parameters such as the dimensions and/or location of extended portion, and the dimensions and/or location of the slab of interest within the extended portion.

As another example, the database module 202 can store data 208c regarding feature spaces associated with each of the MRI protocols. For example, each MRI protocol may be intended to obtain images regarding certain anatomical features of the subject (e.g., one or more particular organs, tissues, structural features, etc. of the subject). Further, each MRI protocol may be designed to produce images that provide contrast between certain types of tissue relative to other types of tissue (e.g., such that certain features of the subject can be distinguished from others visually). Further, each MRI protocol may be intended to investigate the progression of certain disease states or other conditions. Accordingly, for each MRI protocol, the data 208c can store information regarding the corresponding "feature space" of the MRI protocol, such as an indication of the anatomical features that are intended to be imaged by the MRI protocol, the types of tissue that are intended to be distinguished from others using the MRI protocol, and/or the disease states or conditions intended to investigated using the MRI protocol.

As another example, the database module 202 can store data 208d regarding acquisition spaces 208d associated with each of the MRI protocols. For instance, during operation of the MR scanner 102, the MR scanner 102 can obtain measurements regarding the subject according to the frequency domain (often referred to as "k-space" or the "Fourier domain"). In particular, during certain points during an MRI protocol, the MR scanner 102 can measure RF signals emitted by the subject according to multiple "points" in k-space sequentially, where each point corresponds to the measurement of RF signals according to a particular frequency and a particular phase. These sets of points in k-space collectively form an acquisition space for a particular MRI protocol. In some implementations, the acquisition space for an MRI protocol can have a predefined pattern (e.g., a pre-determined set of points, each point corresponding to a different respective frequency and phase). In some implementations, the acquisition space of an MRI protocol can be random or pseudo-random (e.g., a set of points that are randomly or pseudo-randomly distributed in k-space). Further, the acquisition spaces 208d need not be limited solely to k-space. For example, the acquisition spaces 208d can also include patterns of acquisition as defined by one or more non-linear imaging gradients and/or one or more specialized transmit pulses that are generated by the MR scanner 102 (e.g., by the gradient coils 118, or some other signal transmitter), to induce (or otherwise account for) non-linear phase evolution during the imaging process.

As another example, the database module 202 can store data 208e regarding the subjects that were imaged and/or are intended to be imaged by the MR scanner 102. For instance, the data 208e can include, for each subject, the age of the subject, the gender of the subject, demographic information regarding the subject, or other information regarding the subject. Further, the data 208e can include, for each subject, a medical history of the subject (e.g., whether the subject is associated with any disease states or other medical conditions). Further, the data 208e can include, for each subject, information regarding physical characteristics of the subject (e.g., weight, body dimensions, BMI, etc.). Further, the data 208e can include, for each subject, one or more images that were obtained by the subject (e.g., using one or more MRI protocols).

The communications module 204 allows for the transmission of data to and from the MRI training platform 150. For example, the communications module 204 can be communicatively connected to the network 108, such that it can transmit data to and receive data from the computer system 104a. As an example, information from the computer system 104a (e.g., information regarding the operation of the MR scanner 102) can be transmitted to the MRI training platform 150 through the communications module 204. This information can then be processed (e.g., using the processing module 206) and/or stored (e.g., using the database module 202). As another example, information from the MRI training platform 150 (e.g., information stored on the database module 202) can be transmitted to the computer system 104a through communications module 204.

The processing module 206 processes data stored or otherwise accessible to the MRI training platform 150. For instance, the processing module 206 can determine, given a particular MRI protocol, a particular feature space, and a particular subject, a respective parameter set and acquisition space for performing the MRI protocol. In some implementations, the processing module 206 can select a particular parameter set and acquisition space, such that the MRI protocol can be performed in a time-efficient matter and without negatively impact the diagnostic quality of the resulting images (e.g., such that each of the elements of the feature space can be examined for that subject).

In some implementations, the processing module 206 can select a particular parameter set and/or a particular acquisition space automatically (e.g., using one or more machine-learning techniques). For example, the processing module 206 can identify one or more patterns or correlations between the data 208a-208e, and select a particular parameter set and/or a particular acquisition space that is expected to result in images having sufficiently high image quality and/or diagnostic quality. In some implementations, the processing module can select a particular parameter set and/or a particular acquisition space based on human input (e.g., a subjective assessment of sample images by a user).

Further, the processing module 206 can generate instructions for operating the MR scanner 102 (e.g., instructions for operating the MRI scanner 102 according to the MRI protocol, the selected parameter set, and selected acquisition space). The instructions can be provided to another device (e.g., the computer system 104*a*) using the communications module 204 and/or stored for later retrieval via the database module 202.

The processing module 206 can select a particular parameter set and/or a particular acquisition space based on several different factors.

As an example, the processing module 206 can select a particular parameter set based on simulations of the signal response of the subject. For example, the processing module 206 can simulate the RF signal that would be emitted by the subject, given known information regarding the MRI protocol and the subject, and given a particular parameter set and associated values for each of the parameters in the set (e.g., one or more of the parameters described with respect to the data 208*b*). The processing module 206 can determine a quality metric for each parameter set, and select one of the parameter sets based on the quality metrics (e.g., the parameter set having the highest quality metric).

In some implementations, the quality metric can represent the expected image quality and/or the expected diagnostic quality of images produced using the parameter set. For example, a relatively higher quality metric may indicate that the parameter set would produce images having a greater signal to noise ratio (SNR) and/or a greater degree of contrast with respect to a particular feature space, whereas a relatively lower quality metric may indicate that the parameter set would produce images having a lower signal to noise ratio (SNR) and/or a lower degree of contrast with respect to a particular feature space.

In some implementations, the processing module 206 can determine the quality metrics automatically (e.g., without user input). In some implementations, the processing module 206 can determine the quality metrics based, at least in part, on user input (e.g., a subjective assessment of sample images by a user).

In some implementation, the quality metric can be calculated, at least in part, using a cost function. As an example, a cost function can include several components, each corresponding to a respective characteristic of a particular parameter set. Undesirable characteristics can be assigned a greater cost in the cost function, whereas desirable characteristics can be assigned a lower cost in the cost function. Each of these components can be aggregated together (e.g., using a weighted sum or some other combination) to determine a total cost of a parameter set. A parameter set can be selected for use by calculating the total cost for each of several candidate parameter sets, and identifying the candidate parameter set that has the lowest (or an otherwise sufficiently low) cost (e.g., lowest total cost).

As an example, the cost function can include a component that varies in value depending on a fidelity of the acquired data (e.g., signal uniformity across the slab of interest). For instance, the component can have a low value for a parameter set that acquires high fidelity data (e.g., corresponding to a lower cost), and a high value for a parameter set that acquires low fidelity data (e.g., corresponding to a higher cost). This can be beneficial, for example, in favoring parameter sets that produces higher fidelity data over parameter sets that produce lower fidelity data.

In some implementations, the value of this component can be inversely proportional to the fidelity of the acquired data. In some implementations, the value of this component can vary with the fidelity of the acquired data according to some other relationship (e.g., a linear relationship, a non-linear relationship, etc.).

In some implementations, for each parameter set, the fidelity of the acquired data can be determined based on an estimated signal response of the subject responsive to performing the MRI protocol according to that parameter set. In some implementations, the estimated signal response can be determined based on a set of differential equations, such as one or more Bloch equations.

In some implementations, for each parameter set, the fidelity of the acquired data can be determined based on human input (e.g., based on a subjective assessment of sample images by a user).

As another example, the cost function can include a component that varies in value depending on the extent to which the parameter set results in a perturbation of the spins of protons outside a particular region of interest in the subject. For example, as described above, a multi-slab MRI protocol can specify that an MRI scanner 102 obtain information regarding multiple slabs of a subject in a sequence. For these types of MRI protocols, the cost function can include a component that increases in value if the spins of protons outside of the slab (and/or an extended portion enclosing the slab, in the case of MRI protocols employing an oversampling technique) are perturbed to a greater extent. Further, the component can decrease in value if the spins of protons outside of the slab are perturbed to a lesser extent. This can be beneficial, for example, in favoring parameter sets that avoid or otherwise reduce a perturbation of spins outside a region of interest (which may enhance image quality) over parameter sets that would cause a greater extent of perturbation of spins outside a region of interest (which may reduce image quality).

In some implementations, the value of this component can be inversely proportional to the extent to which proton spins are perturbed outside a particular region of interest. In some implementations, the value of this component can vary with the extent to which proton spins are perturbed outside a particular region of interest according to some other relationship (e.g., a linear relationship, a non-linear relationship, etc.).

In some implementations, for each parameter set, proton spin perturbation can be determined based on an estimated signal response of the subject responsive to performing the MRI protocol according to that parameter set. In some implementations, the estimated signal response can be determined based on a set of differential equations, such as one or more Bloch equations.

As another example, the cost function can include a component that varies in value depending on the extent to which the parameter set results in an excitation of protons outside a particular region of interest in the subject. For example, as described above, a multi-slab MRI protocol can specify that an MRI scanner 102 obtain information regarding multiple slabs of a subject in a sequence. For these types of MRI protocols, the cost function can include a component that increases in value if protons outside of the slab (and/or an extended portion enclosing the slab, in the case of MRI protocols employing an oversampling technique) are excited to a greater extent. Further, the component can decrease in value if the protons outside of the slab are excited to a lesser extent. This can be beneficial, for example, in favoring parameter sets that avoid or otherwise reduce an excitation of protons outside a region of interest (which may enhance image quality) over parameter sets that cause a greater extent of excitation of protons outside a region of interest (which may reduce image quality).

In some implementations, the value of this component can be inversely proportional to the extent to which protons are excited outside a particular region of interest. In some implementations, the value of this component can vary with the extent to which protons are excited outside a particular region of interest according to some other relationship (e.g., a linear relationship, a non-linear relationship, etc.).

In some implementations, for each parameter set, proton excitation can be determined based on an estimated signal response of the subject responsive to performing the MRI protocol according to that parameter set. In some implementations, the estimated signal response can be determined based on a set of differential equations, such as one or more Bloch equations.

As described above, in some implementations, each of the components of the cost function can be aggregated together to determine a total cost of a parameter set. In some implementations, the components of the cost function can be aggregated together according to a weighted sum. Further, the weights of the component can be selected to define the influence of each component on the overall cost. In some implementations, the weights can be selected empirically. In some implementations, the components of the cost function can be aggregated according to a non-linear relationship.

Further, as described above, a parameter set can be selected for use by calculating the cost for each of several candidate parameter sets, and identifying the candidate parameter set that has the lowest (or an otherwise sufficiently low) cost (e.g., lowest total cost). In some implementations, a parameter set can be selected by determining the minimization of the cost function, such as using the Levenberg-Marquardt algorithm or dampened least-squares (DLS) method.

In some implementation, the quality metric of a particular parameter set can be inversely related to the cost for that parameter set. In some implementations, the quality metric can vary with the cost according to some other relationship (e.g., a linear relationship, a non-linear relationship, etc.).

In some implementations, the processing module 206 can select a particular acquisition space to improve upon traditional compressed sensing (CS) techniques. For instance, in CS techniques, images can be reconstructed by acquiring substantially fewer data points (e.g., in k-space) than the number of voxels that are present in the image. In particular, the image space is transformed into a sparse domain (e.g., with most of the data points zero). Data points are randomly sampled in the acquisition space (which is, in general, not equivalent to the image space). As a closed-form solution for the reconstruction does not exist, an iterative reconstruction procedure is used, which is a trade-off between optimization of data fidelity (e.g., how well the image matches the acquired data) and data sparsity (e.g., how sparse the image is in the sparse domain). However, traditional CS techniques may be suboptimal in at least some use cases, as it does not incorporate prior knowledge about the anatomy. Moreover, images may not be available in real-time for a clinician, given the amount of time needed to generate the images.

To address these issues, the processing module 206 may dynamically specify the sparse domain to enhance clinically relevant information, while deemphasizing or discarding other extraneous information. In some implementations, this can be performed, at least in part, by selecting an acquisition space that is determined to result in a relatively lower degree of image compression in one or more regions of interest in a subject, and a relatively greater degree of image compression in one or more other regions in a subject that are of lesser interest. For instance, in a brain scan, the acquisition space can be selected such that the portions of the images corresponding to the cerebrum and the cerebellum are subject to relatively lower degree of image compression, whereas the portions of the images corresponding to other areas that are not of clinical interest (e.g., the neck and the eyes) are subject to relatively greater degree of image compression.

Further, the processing module 206 can dynamically select an acquisition space according to an under-sampling scheme that is specific to the MRI protocol, the feature space, and/or the subject. For example, in a traditional CS technique, measurements are acquired according to random or pseudo-random under-sampling scheme in the acquisition domain (e.g., "k-space"). This may be effective in some implementations, for example, when there is no prior information regarding the MRI protocol, the feature space, and/or the subject. For instance, without any prior knowledge, there may not be any reason to expect that a particular data point in the acquisition domain will carry more or less information than any other data point. Accordingly, an optimal acquisition scheme may maximize orthogonality in the acquisition domain. However, in reality, each data point in the acquisition domain may carry different amounts of information. Accordingly, given certain known information regarding the MRI protocol, the feature space, and/or the subject, the processing module 206 can select a specific set of data points in the acquisition domain (e.g., a specific acquisition space) that prioritizes the acquisition of data points that carry relatively more clinically-relevant information. Accordingly, measurements can be acquired in a time-efficient matter and without negatively impact the diagnostic quality of the resulting images.

Further, the processing module 206 can modify a MRI protocol by incorporating one or more non-linear imaging gradients into a particular pulse sequence specified by the MRI protocol. For example, a MRI protocol may specify that the MR generate one or more magnetic field gradients within a subject (e.g., a magnetic field that varies spatially) using the gradient coils. Accordingly, different portions of the subject will be subjected to different magnetic field strengths, depending on their spatial location. As protons process (e.g., "wobble" about an axis) according to a frequency that depends on the magnetic field strength, the protons of the subject will correspondingly process according to different frequencies, depending on their spatial location. The MR scanner can selectively acquire data regarding a specific portion of the subject by applying RF energy having a frequency corresponding to that portion of the subject (e.g., such that only the protons in that portion are excited), and measuring the RF signal emitted by the protons in that portion of the subject. In some implementations, the processing module 206 can select one or more magnetic field gradients that vary non-linearly across the subject. For example, the processing module 206 can select a higher gradient for regions where relatively greater spatial resolution is desired (e.g., which enables the MR scanner to selectively excite protons with a greater degree of precision spatially), and lower gradients in regions where the spatial resolution is less of a concern. In some implementations, the magnetic field gradient have vary spatially according to a non-linear equation, such as a quadratic equation.

Further, the processing module 206 can reconstruct images (or instruct another computer system to reconstruct images) based on prior information regarding the data acquisition process. For example, a typical CS technique (which does not rely on known information), images are reconstructed according to an iterative process, which may be computationally intensive and time consuming to perform. This may be less desirable to a clinical setting, which may require that images be available for viewing in real-time or substantially real-time. This problem can be ameliorated by determining, based on known information regarding the data acquisition process, a closed form reconstruction that approximates the "optimum" solution to the reconstruction. Accordingly, the optimum solution to the reconstruction can be identified using fewer iterations.

In some implementations, the MRI training platform 150 can also select sets of parameters pertaining to a MRI protocols in which multiple three-dimensional slabs are excited simultaneously.

In some implementations, a MRI protocol can instead specify that a MR scanner simultaneously excite multiple three-dimensional slabs (rather than two-dimensional slices). According to this protocol, the resulting image is the sum of multiple slabs. However, due to the three-dimensional nature of the imaging protocol, corresponding slices are not aligned between the slabs. Therefore, using an arbitrary choice of CAIPINRHA gradient or blipped-CAIPI gradient will result in desired shifts for some slices but not others.

As an illustrative example, a MRI protocol can specify that an MR scanner simultaneously excite three slabs, with a 10 mm slab of interest, a 12 mm imaged slab (20% oversampling), 50 mm between slabs, a 1 mm desired slice thickness, and 170 points in a first phase-encoding direction.

In this example, the slices can be reconstruct ordered according to the table below.

TABLE 1

Example slice reconstruction order.

| | | Slice Number | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Slab Number | 1 | −54 | −53 | −52 | −51 | −50 | −49 | −48 | −47 | −46 | −45 | −56 | −55 |
| | 2 | −6 | −5 | −4 | −3 | −2 | −1 | 0 | 1 | 2 | 3 | 4 | 5 |
| | 3 | 54 | 55 | 44 | 45 | 46 | 47 | 48 | 49 | 50 | 51 | 52 | 53 |

Values refer to the position (in mm) for each slice, assuming slabs are centered ta −50 mm, 0 mm, and 50 mm relative to a reference point or reference plane).

In general, according to some MRI protocols (e.g., simultaneous-multi-slice (SMS) protocols, also called multi-band (MB) protocols), two or more slices can be excited simultaneously. For instance, a MRI protocol can specify that a MR scanner simultaneously excite a first slice at a first position on the subject (e.g., 0 mm from a reference point or reference plane) and second slice at a second position on the subject (e.g., 40 mm from the reference point or reference plane). The resulting image that is obtained by the MR scanner is the sum of the two slices. Further, the MR scanner can leverage differences in the sensitives of its coils to separate (or "unalias") the two slices from one another.

In some implementations, the quality of the images can be further improved by shifting one slice (e.g., the upper slice relative to the reference point or reference plane) in the phase-encoding direction (e.g., Y-direction) by applying an appropriate gradient in the slice direction (e.g., Z-direction) together with the normal phase-encoding gradients in the Y-direction. The Z-direction gradient strength can be chosen appropriately such that the upper image will shift an integer number of voxels, and is inversely proportional to the distance between the slices (e.g., using a technique such as Controlled Aliasing in Parallel Imaging Results in Higher Acceleration (CAIPINRHA) or Blipped-Controlled Aliasing in Parallel Imaging (blipped-CAIPI). This gradient may be referred to as a CAIPINRHA gradient or a blipped-CAIPI gradient. In at least some implementations, this condition enables unaliasing to be performed in a computationally efficient manner (e.g., by lessening the computational resources, such as CPU utilization, that would be required to perform the unaliasing process). However, if the gradient strength is incorrect chosen, unaliasing may be computationally demanding to perform, as the result is no longer a simple shift in the Y-direction.

Thus, the distance between corresponding slices is sometimes 48 mm and sometimes 60 mm. In this example, choosing a correct CAIPINRHA gradient or blipped-CAIPI gradient for the slice at 48 mm will not yield the correct result for the slice at 60 mm. This may make unaliasing computationally demanding to perform.

The MRI training platform 150 can select specific sets of parameters to reduce the computational overhead of performing the unaliasing process. For instance, in the example above, choosing a shift of 85 voxels (e.g., equal to one half of the field of view, FOV) for a 48 mm separation results in two shifted images in the case of a 60 mm separation, resulting in only one extra parameter in the forward transformation.

The MRI training platform 150 can select sets of parameters that enable unaliasing to be performed in a computationally efficient manner. For example, the MRI training platform 150 can select parameters such as the thickness of each slab, the degree of which a slab is oversampled (e.g., an oversampling factor), the distance between slabs, and the number of sample points in the first phase-encoding direction (e.g., Y-direction). In some implementations, at least some of these parameters can be included in the parameter sets 208b (e.g., described with reference to FIG. 2), and MRI training platform 150 can select values for at least some of these parameters using the techniques described above (e.g., based on simulated RF signals, quality metrics, cost functions, human input, or combinations thereof).

In some implementations, the MRI training platform 150 can also select values for at least some of these parameters based, at least in part, on the amount of computational resources (e.g., CPU utilization) that would be consumed to process data obtained using those parameters (e.g., unaliasing).

In some implementations, the MRI training platform 150 can also select values for at least some of these parameters based at least in part, on an estimation of the amount of computational resources (e.g., CPU utilization) that would be consumed to process data obtained using those parameters (e.g., unaliasing). This estimate can be determined, for example, based on computation simulations.

Example Processes

Figure 3A:
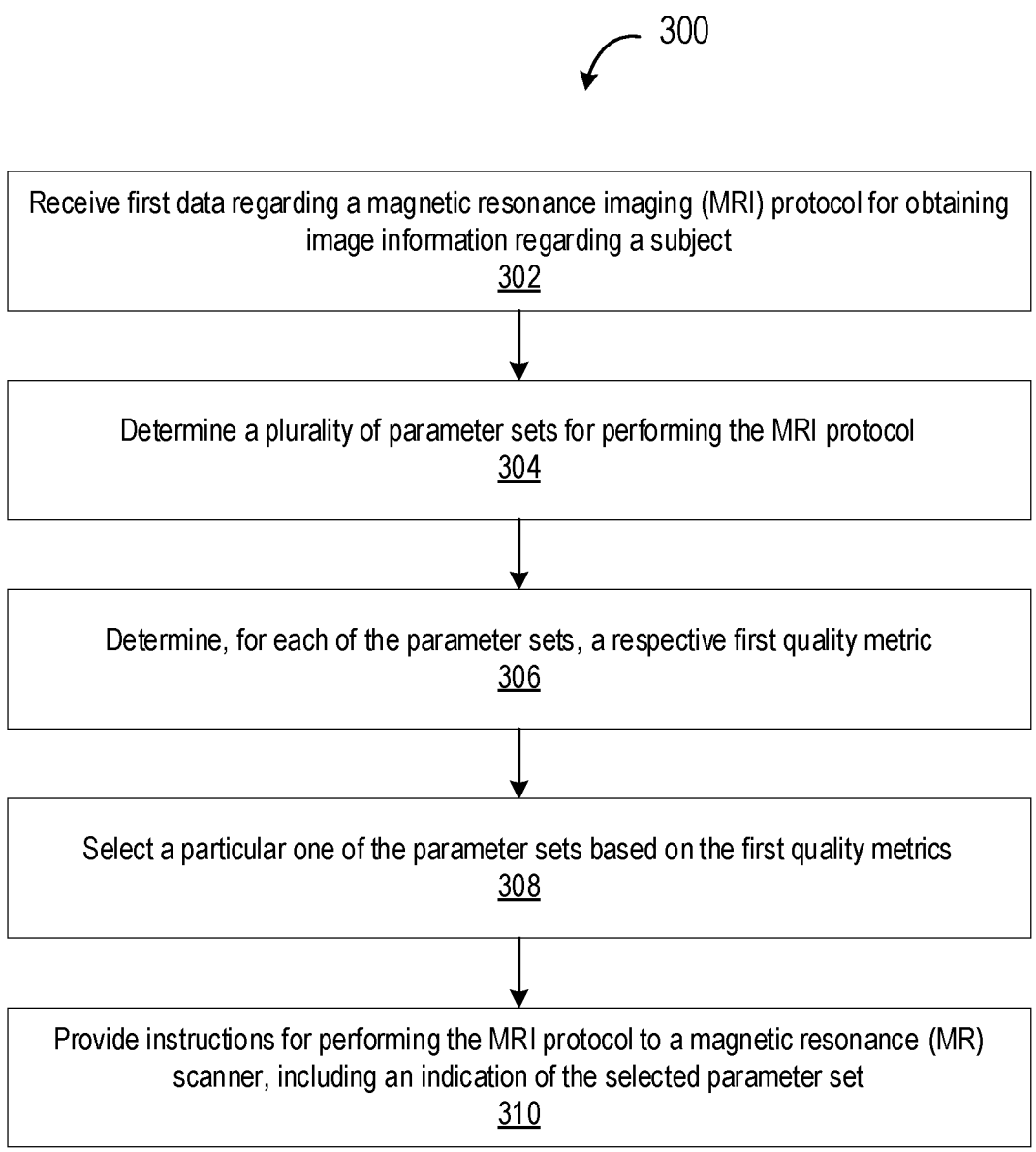
FIGS. 3A-3C are flow diagrams of example processes for performing an MRI protocol.

An example process 300 for performing an MRI protocol is shown in FIG. 3A. In some implementations, the process 300 can be performed by the system 100 in FIG. 1 and/or the training platform 150 shown in FIG. 2.

In the process 300, a computer system receives first data regarding a magnetic resonance imaging (MRI) protocol for obtaining image information regarding a subject (block 302).

In some implementations, the first data can include an indication of a medical condition of the subject (e.g., whether the subject is associated with any disease states or other medical conditions). In some implementations, the first data can include an indication of a type of image contrast associated with the MRI protocol (e.g., T1-weighted contrast, T2-weighted contrast, diffusion-weighted contrast, and/or any other type of contrast). In some implementations, the first data can include an indication of a magnetic resonance (MR) pulse sequence associated with the MRI protocol. In some implementations, the first data can include one or more of the data 208a-208e described with respect to FIG. 2.

The computer system determines a plurality of parameter sets for performing the MRI protocol (block 304). Each of the parameter sets includes an indication of one or more parameters associated with the MRI protocol. Further, each of the parameter sets includes, for each of the one more parameters, an indication of a respective parameter value.

Example parameters include a field of view (FOV), a matrix size, a slice thickness, a repetition time (TR), an echo time (TE), an inversion time (TI), a flip angle (FA), a magnetic gradient strength, a magnetic gradient duration, a radio frequency (RF) transmit power, a time-bandwidth product, and an averaging of acquired data. Another example parameter includes a shape of a pulse in a pulse sequence of the MRI protocol. The shape of the pulse can include a duration of the pulse and/or a magnitude of the pulse. Further example parameters include a number of slabs from which to obtain the image information regarding the subject, an acquisition sequence for the slabs, a spacing between the slabs, a thickness of the slabs, an oversampling factor for the slabs, or a number of sample points in a phase-encoding direction. A parameter set can include any combination of parameters and corresponding parameter values.

The computer system determines, for each of the parameter sets, a respective first quality metric (block 306). Example techniques for determining the first quality metrics are described herein. For instance, the computer system can simulate the RF signal that would be emitted by the subject, given known information regarding the MRI protocol and the subject, and given a particular parameter set and associated values for each of the parameters in the set. The computer system can determine a first quality metric for each parameter set, and select one of the parameter sets based on the first quality metrics (e.g., the parameter set having the highest first quality metric). In some implementations, the first quality metric can represent the expected image quality and/or the expected diagnostic quality of images produced using the parameter set. In some implementations, the computer system determine the first quality metrics automatically (e.g., without user input). In some implementations, the computer system can determine the first quality metrics based, at least in part, on user input (e.g., a subjective assessment of sample images by a user).

As an example, for each of the parameter sets, the computer system can determine an estimated signal response of the subject responsive to performing the MRI protocol according to that parameter set. In some implementations, the estimated signal response can be determined based on a set of differential equations, such as one or more Bloch equations. Further, for each of the parameter sets, the computer system can determine one or more first properties of the estimated signal response, and an estimated duration of time for performing the MRI protocol according to that parameter set. In some implementations, the one or more first properties can include a contrast to noise ratio of the estimated signal response and/or a signal to noise ratio of the estimated signal response. The computer system can determine the first quality metric for that parameter set based on the one or more first properties of the estimated signal response and the estimated duration of time.

In some implementations, the first quality metrics can be determined based on a cost function. As an example, a cost function can include a plurality of components. Further, the components can include, for each of the parameter sets, (i) a first component corresponding to a fidelity of data acquired according to that parameter sets, (ii) a second component corresponding to a perturbation of proton spins outside a region of interest specified by that parameter set, and/or (iii) a second component corresponding to an excitation of proton outside the region of interest specified by that parameter set.

Further, in some implementations, the cost function can include a weighted sum of the components.

Further, in some implementations, for each of the parameter sets, a respective first quality metric can be determined by determining an output of the cost function for that parameter set.

The computer system selects a particular one of the parameter sets based on the first quality metrics (block 308). In some implementations, the parameter set having the greatest first quality metric among the first quality metrics can be selected. In some implementations, a parameter set having a first quality metric that exceeds a threshold value can be selected. In some implementations, the threshold value can be selected empirically (e.g., based on experimental studies).

In some implementations, the particular one of the parameter sets can be selected by selecting, from among the parameter sets, the parameter set associated with the lowest output of the cost function.

In some implementations, the particular one of the parameter sets can selected by selecting, from among the parameter sets, the parameter set associated with the lowest outputted value of the cost function.

The computer system provides instructions for performing the MRI protocol to a magnetic resonance (MR) scanner (block 310). The instructions include an indication of the selected parameter set. As an example, the instructions can include an indication to perform the MRI protocol according to a particular set of parameters and the selected parameter values.

Figure 3B:
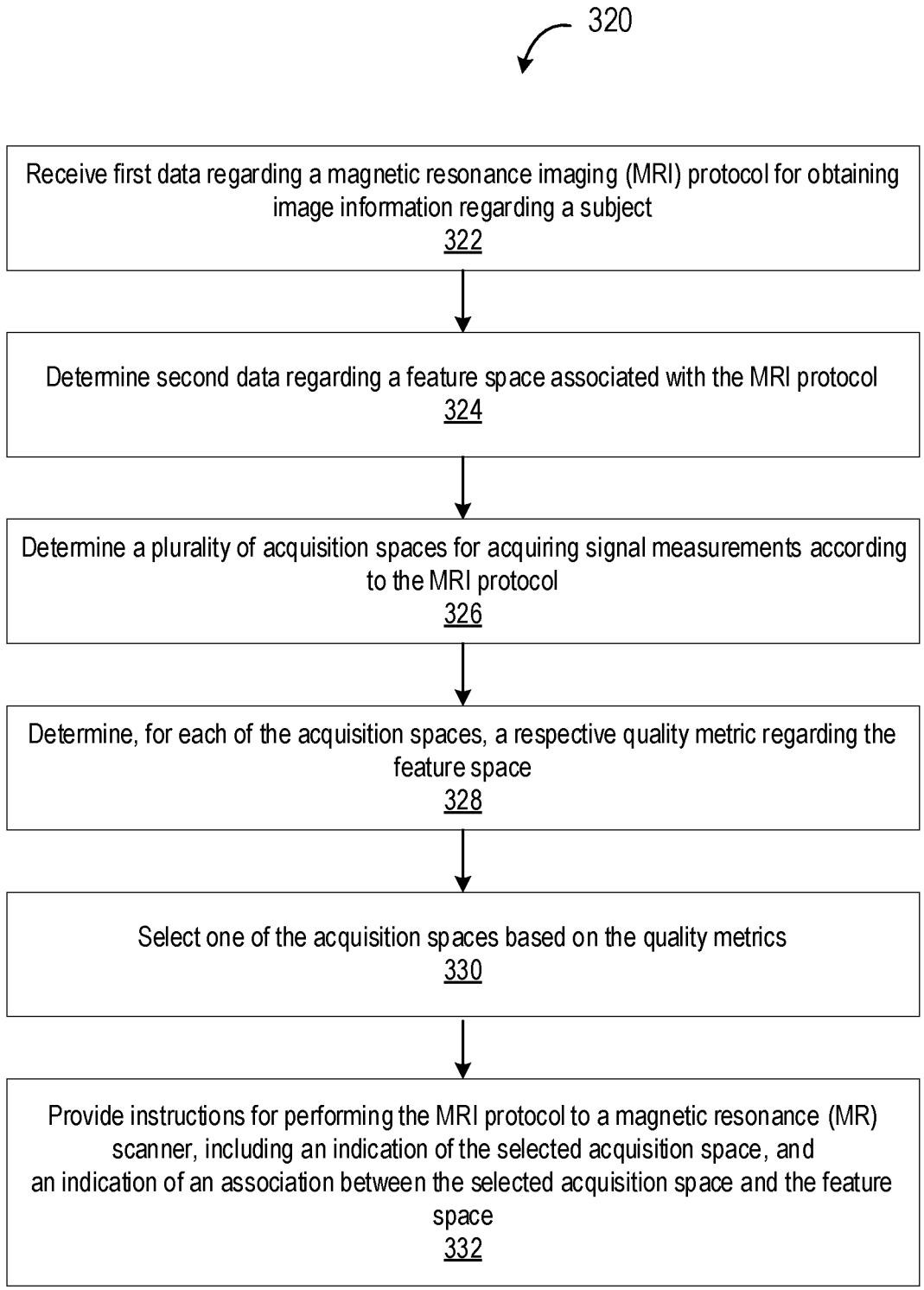

Another example process 320 for performing an MRI protocol is shown in FIG. 3B. In some implementations, the process 320 can be performed by the system 100 in FIG. 1 and/or the training platform 150 shown in FIG. 2.

In the process 320, a computer system receives first data regarding a magnetic resonance imaging (MRI) protocol for obtaining image information regarding a subject (block 322).

In some implementations, the first data can include an indication of a medical condition of the subject (e.g., whether the subject is associated with any disease states or other medical conditions). In some implementations, the first data can include an indication of a type of image contrast associated with the MRI protocol (e.g., T1-weighted contrast, T2-weighted contrast, diffusion-weighted contrast, and/or any other type of contrast). In some implementations, the first data can include an indication of a magnetic resonance (MR) pulse sequence associated with the MRI protocol. In some implementations, the first data can include one or more of the data 208a-208e described with respect to FIG. 2.

The computer system determines second data regarding a feature space associated with the MRI protocol (block 324). In some implementations, the feature space can include one or more anatomical features of the subject and/or one or more types of tissue of the subject.

The computer system determines a plurality of acquisition spaces for acquiring signal measurements according to the MRI protocol (block 326). In some implementations, at least one of the acquisition spaces can include a respective pattern of sample points in k-space. In some implementations, at least one of the acquisition spaces can include a respective pattern of sample points acquired using one or more non-linear imaging gradients or transmit pulses (e.g., to induce or otherwise account for non-linear phase evolution during the imaging process).

The computer system determines, for each of the acquisition spaces, a respective quality metric regarding the feature space (block 328). Example techniques for determining the quality metrics are described herein. For instance, the computer system can dynamically specify a sparse domain to enhance clinically relevant information, while deemphasizing or discarding other extraneous information. In some implementations, this can be performed, at least in part, by selecting an acquisition space that is determined to result in a relatively lower degree of image compression in one or more regions of interest in a subject, and a relatively greater degree of image compression in one or more other regions in a subject that are of lesser interest. Further, the computer system can dynamically select an acquisition space according to an under-sampling scheme that is specific to the MRI protocol, the feature space, and/or the subject. Further, the computer system can modify a MRI protocol by incorporating one or more non-linear imaging gradients into a particular pulse sequence specified by the MRI protocol.

The quality metrics can be used to quantify the quality of the images obtained by each of the acquisition spaces. For example, each quality metric can represent the expected image quality and/or the expected diagnostic quality of images produced using a particular acquisition space. In some implementations, the computer system determine the first metrics automatically (e.g., without user input). In some implementations, the computer system can determine the quality metrics based, at least in part, on user input (e.g., a subjective assessment of sample images by a user).

As an example, for each of the acquisition spaces, the computer system can obtaining image data corresponding to a performance of the MRI protocol according to that acquisition space, and determine one or more properties of the image data with respect to the feature space. In some implementations, the one or more properties of the image data can include a contrast to noise ratio with respect to the feature space and/or a signal to noise ratio with respect to the feature space. In some implementations, the one or more properties of the image data can include a qualitative score regarding the feature space (e.g., received from one or more users). The computer system can determine the quality metric for that acquisition space based on the one or more properties of the image data.

The computer system selects one of the acquisition spaces based on the quality metrics (block 330). In some implementations, the acquisition space having the greatest quality metric among the quality metrics can be selected. In some implementations, an acquisition space having a quality metric that exceeds a threshold value can be selected. In some implementations, the threshold value can be selected empirically (e.g., based on experimental studies).

The computer system, provides instructions for performing the MRI protocol to a magnetic resonance (MR) scanner (block 332). The instructions include an indication of the selected acquisition space, and an indication of an association between the selected acquisition space and the feature space. As an example, the instructions can include an indication to perform the MRI protocol according to the selected acquisition space and according to the specified feature space.

Figure 3C:
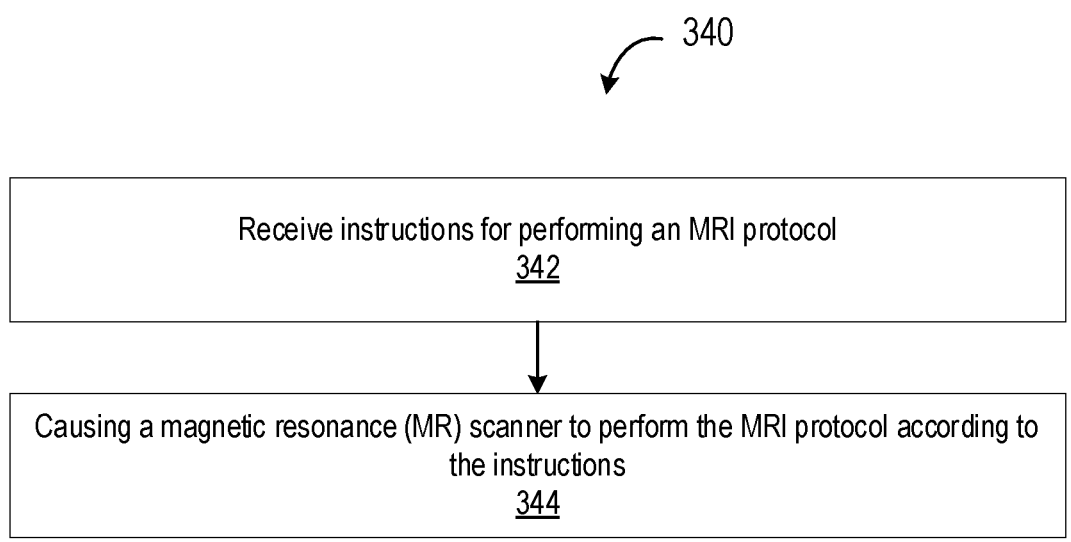

Another example process 340 for performing an MRI protocol is shown in FIG. 3C. In some implementations, the process 340 can be performed by the system 100 in FIG. 1 and/or the training platform 150 shown in FIG. 2.

In the process 340, a first computer system receives instructions for performing an MRI protocol from a second computer system (block 342). As an example, the first computer system can be the computer system 104a shown in FIG. 1, and the second computer system can be the computer system 104b shown in FIG. 1.

The instructions can be generated using one or more of the techniques described herein. For example, the instructions can include an indication of a particular parameter set selected from among a plurality of parameter sets by the second computer system. The particular parameter set can be selected by determining the plurality of parameter sets for performing the MRI protocol. Each of the parameter sets can include an indication of one or more parameters associated with the MRI protocol, and for each of the one more parameters, an indication of a respective parameter value. Further, a respective first quality metric can be determined for each of the parameter sets. A particular one of the parameter sets can be selected based on the first quality metrics.

As another example, the instructions can include an indication of a particular acquisition space for performing the MRI protocol, and an indication of an association between the particular acquisition space and a feature space associated with the MRI protocol. The particular parameter set can be selected by determining second data regarding the feature space, a plurality of acquisition spaces for acquiring signal measurements according to the MRI protocol. For each of the acquisition spaces, a respective second quality metric regarding the feature space can be determined. A particular acquisition space from among the plurality of acquisition spaces can be selected based on the second quality metrics.

Additional techniques for generating instructions are described herein (e.g., with respect to FIGS. 2, 3A, and 3B).

The first computer system causes a magnetic resonance (MR) scanner to perform the MRI protocol according to the instructions (block 344). For example, referring to FIG. 1, the computer system 104a can instruct the MR scanner 102 to execute perform the MRI protocol specified by the instructions.

Although the processes 300, 320, and 340 are illustrated separately, in some implementations, some or all of these processes can be performed as a part of a single overall process. For example, some or all of the processes 300 and/or 320 can be performed to generate instructions from an MR scanner, and some or all of the process 340 can be performed to cause the MR scanner to perform an MRI protocol in accordance with those instructions.

Example Systems

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the computer system 104a and 104b, the MRI training platform 150, and the MR scanner 102 can be implemented using digital electronic circuitry, or in computer software, firmware, or hardware, or in combinations of one or more of them. In another example, the processes 300, 320, and 340 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 4:
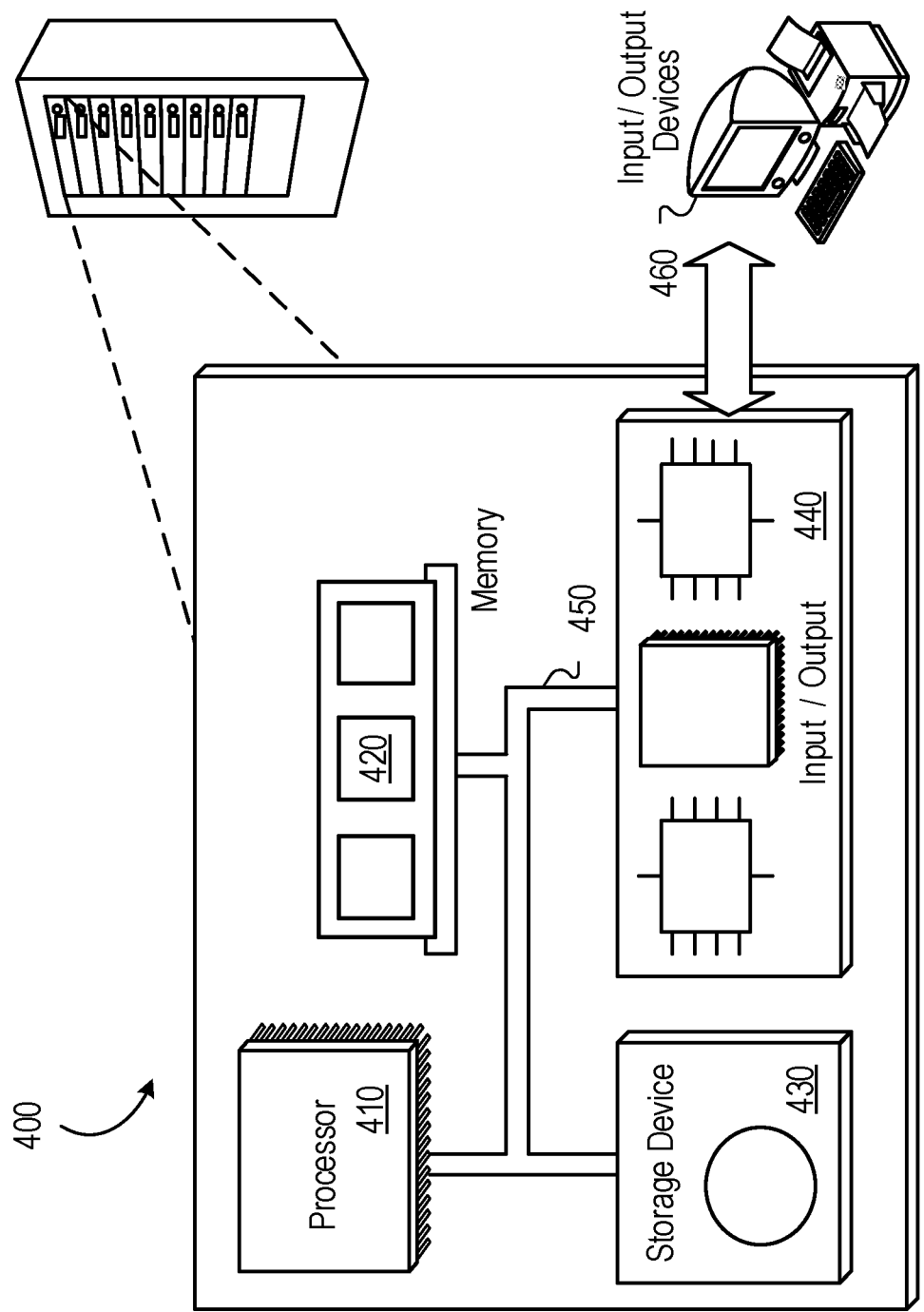
FIG. 4 is a diagram of an example computer system.

FIG. 4 shows an example computer system 400 that includes a processor 400, a memory 420, a storage device 430 and an input/output device 440. Each of the components 410, 420, 430 and 440 can be interconnected, for example, by a system bus 450. The processor 410 is capable of processing instructions for execution within the system 400. In some implementations, the processor 410 is a single-threaded processor, a multi-threaded processor, or another type of processor. The processor 410 is capable of processing instructions stored in the memory 420 or on the storage device 430. The memory 420 and the storage device 430 can store information within the system 400.

The input/output device 440 provides input/output operations for the system 400. In some implementations, the input/output device 440 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 460. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of implementations have been described. Nevertheless, it will be understood that various modifications may be made without departing from the spirit and scope of the invention. Accordingly, other implementations are within the scope of the following claims.

What is claimed is:

1. A method comprising:
   receiving, by a computer system, first data regarding a magnetic resonance imaging (MRI) protocol for obtaining image information regarding a subject;
   determining, by the computer system, a plurality of parameter sets for performing the MRI protocol, wherein each of the parameter sets comprises:
   (i) an indication of one or more parameters associated with the MRI protocol, and
   (ii) for each of the one more parameters, an indication of a respective parameter value;
   determining, by the computer system and for each of the parameter sets, a respective first quality metric, wherein the first quality metrics are determined based on one or more components associated with each of the parameters, wherein the components comprise, for each of the parameter sets, at least one of:
   a first component corresponding to a perturbation of proton spins outside a region of interest specified by that parameter set, or
   a second component corresponding to an excitation of proton outside the region of interest specified by that parameter set;
   selecting, by the computer system, a particular one of the parameter sets based on the first quality metrics; and
   providing, by the computer system, instructions for performing the MRI protocol to a magnetic resonance (MR) scanner, wherein the instructions comprise an indication of the selected parameter set.

2. The method of claim 1, wherein the first data comprises at least one of:
   an indication of a medical condition of the subject, or
   an indication of a type of image contrast associated with the MRI protocol.

3. The method of claim 2, wherein the first data comprises an indication of a type of image contrast associated with the MRI protocol.

4. The method of claim 3, wherein the type of image contrast is at least one of a T1-weighted contrast, a T2-weighted contrast, or a diffusion-weighted contrast.

5. The method of claim 1, wherein the first data comprises an indication of a magnetic resonance (MR) pulse sequence associated with the MRI protocol.

6. The method of claim 1, wherein the one or more parameters associated with the MRI protocol comprise at least one of:
   a field of view,
   a matrix size,
   a slice thickness,
   a repetition time,
   an echo time,
   an inversion time,
   a flip angle,
   a magnetic gradient strength,
   a magnetic gradient duration,
   a radio frequency (RF) transmit power,
   a time-bandwidth product, or
   an averaging of acquired data.

7. The method of claim 1, wherein the one or more parameters associated with the MRI protocol comprise a shape of a pulse in a pulse sequence of the MRI protocol.

8. The method of claim 7, wherein the shape of the pulse comprises at least one of:
   a duration of the pulse, or
   a magnitude of the pulse.

9. The method of claim 1, wherein the one or more parameters associated with the MRI protocol comprise at least one of:
   a number of slabs from which to obtain the image information regarding the subject,
   an acquisition sequence for the slabs,
   a spacing between the slabs,
   a thickness of the slabs,
   an oversampling factor for the slabs, or
   a number of sample points in a phase-encoding direction.

10. The method of claim 1, wherein determining the first quality metrics comprises:
    for each of the parameter sets:
      determining an estimated signal response of the subject responsive to performing the MRI protocol according to that parameter set,
      determining one or more first properties of the estimated signal response, determining an estimated duration of time for performing the MRI protocol according to that parameter set, and determining the first quality metric for that parameter set based on the one or more first properties of the estimated signal response and the estimated duration of time.

11. The method of claim 10, wherein the one or more first properties comprise least one of:
a contrast to noise ratio of the estimated signal response, or
a signal to noise ratio of the estimated signal response.

12. The method of claim 10, wherein the estimated signal response is determined based on a set of differential equations.

13. The method of claim 12, wherein the set of differential equations comprises Bloch equations.

14. The method of claim 1, wherein first quality metrics are determined based on a cost function.

15. The method of claim 14, wherein the components comprise, for each of the parameter sets:
a third component corresponding to a fidelity of data acquired according to that parameter sets.

16. The method of claim 15, wherein the cost function comprises a weighted sum of the components.

17. The method of claim 14, wherein determining, for each of the parameter sets, a respective first quality metric comprises:
determining, for each of the parameter sets, an output of the cost function for that parameter set.

18. The method of claim 17, wherein selecting the particular one of the parameter sets comprises:
selecting, from among the parameter sets, the parameter set associated with the lowest output of the cost function.

19. The method of claim 14, wherein selecting the particular one of the parameter sets comprises:
selecting, from among the parameter sets, the parameter set associated with the lowest outputted value of the cost function.

20. The method of claim 1, wherein selecting a particular one of the parameter sets comprises selecting the parameter set having the greatest first quality metric among the first quality metrics.

21. The method of claim 1, wherein selecting a particular one of the parameter sets comprises selecting a parameter set having a first quality metric that exceeds a threshold value.

22. The method of claim 1, further comprising:
determining, by the computer system, second data regarding a feature space associated with the MRI protocol;
determining, by the computer system, a plurality of acquisition spaces for acquiring signal measurements according to the MRI protocol;
determining, by the computer system for each of the acquisition spaces, a respective second quality metric regarding the feature space; and
selecting, by the computer system, one of the acquisition spaces based on the second quality metrics,
wherein the instructions further comprise:
an indication of the selected acquisition space, and
an indication of an association between the selected acquisition space and the feature space.

23. The method of claim 22, wherein the feature space comprises at least one of:
one or more anatomical features of the subject, or one or more types of tissue of the subject.

24. The method of claim 22, wherein at least one of the acquisition spaces comprises a respective pattern of sample points in k-space.

25. The method of claim 22, wherein at least one of the acquisition spaces comprises a respective pattern of sample points acquired using one or more non-linear imaging gradients or transmit pulses.

26. The method of claim 22, wherein determining the second quality metrics comprises:
for each of the acquisition spaces,
obtaining image data corresponding to a performance of the MRI protocol according to that acquisition space,
determining one or more second properties of the image data with respect to the feature space, and
determining the second quality metric for that acquisition space based on the one or more second properties of the image data.

27. The method of claim 26, wherein the one or more second properties of the image data comprises at least one of:
a contrast to noise ratio with respect to the feature space, or
a signal to noise ratio with respect to the feature space.

28. The method of claim 26, wherein the one or more second properties of the image data comprises a qualitative score regarding the feature space.

29. The method of claim 28, wherein the qualitative score is received from one or more users.

30. The method of claim 22, wherein selecting one of the acquisition spaces comprises selecting the acquisition space having the greatest second quality metric among the second quality metrics.

31. The method of claim 22, wherein selecting one of the acquisition spaces comprises selecting an acquisition space having a second quality metric that exceeds a threshold value.

32. The method of claim 1, wherein for each of the parameter sets, the components comprise the first component and the second component.

33. The method of claim 1, wherein the first quality metrics are determined based on a cost function comprising a weighted sum of at least the first component and the second component.

34. A system comprising:
one or more processors; and
one or more non-transitory computer readable media storing instructions that, when executed by the one or more processors, cause the one or more processors to perform operations comprising:
receiving first data regarding a magnetic resonance imaging (MRI) protocol for obtaining image information regarding a subject;
determining a plurality of parameter sets for performing the MRI protocol, wherein each of the parameter sets comprises:
(i) an indication of one or more parameters associated with the MRI protocol, and
(ii) for each of the one more parameters, an indication of a respective parameter value;
determining, for each of the parameter sets, a respective first quality metric,
wherein the first quality metrics are determined based on one or more components associated with each of the parameters, wherein the components comprise, for each of the parameter sets, at least one of:

a first component corresponding to a perturbation of proton spins outside a region of interest specified by that parameter set, or a second component corresponding to an excitation of proton outside the region of interest specified by that parameter set;

selecting a particular one of the parameter sets based on the first quality metrics; and providing instructions for performing the MRI protocol to a magnetic resonance (MR) scanner, wherein the instructions comprise an indication of the selected parameter set.

35. One or more non-transitory computer readable media storing instructions that, when executed by one or more processors, cause the one or more processors to perform operations comprising:

receiving first data regarding a magnetic resonance imaging (MRI) protocol for obtaining image information regarding a subject;

determining a plurality of parameter sets for performing the MRI protocol, wherein each of the parameter sets comprises:

(i) an indication of one or more parameters associated with the MRI protocol, and (ii) for each of the one more parameters, an indication of a respective parameter value;

determining, for each of the parameter sets, a respective first quality metric, wherein the first quality metrics are determined based on one or more components associated with each of the parameters, wherein the components comprise, for each of the parameter sets, at least one of:

a first component corresponding to a perturbation of proton spins outside a region of interest specified by that parameter set, or a second component corresponding to an excitation of proton outside the region of interest specified by that parameter set;

selecting a particular one of the parameter sets based on the first quality metrics; and providing instructions for performing the MRI protocol to a magnetic resonance (MR) scanner, wherein the instructions comprise an indication of the selected parameter set.

* * * * *